(12) United States Patent
Nosaka et al.

(10) Patent No.: US 6,395,741 B1
(45) Date of Patent: May 28, 2002

(54) AGENT FOR PROPHYLAXIS OR TREATMENT OF DYSURIA

(75) Inventors: Kunio Nosaka, Kasukabe; Koichiro Yamada, Saitama-ken, both of (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/672,015

(22) Filed: Sep. 29, 2000

Related U.S. Application Data

(63) Continuation of application No. PCT/JP99/01614, filed on Mar. 30, 1999.

(30) Foreign Application Priority Data

Mar. 31, 1998 (JP) ............................................ 10-086012

(51) Int. Cl.[7] ...................... A61K 31/505; A61K 31/497
(52) U.S. Cl. .............. 514/269; 514/252.02; 514/252.14
(58) Field of Search ................................ 544/319, 295, 544/296; 514/269, 252.02, 252.14

(56) References Cited

U.S. PATENT DOCUMENTS

| 5,589,478 A | 12/1996 | Yamada et al. .............. 514/269 |
| 5,760,038 A | 6/1998 | Murugesan et al. ......... 514/252 |
| 5,883,092 A | 3/1999 | Hirata et al. .............. 514/235.8 |

FOREIGN PATENT DOCUMENTS

| EP | 0 768 305 | 4/1997 |
| JP | 09-059160 | 3/1997 |
| WO | 94/21590 | 9/1994 |
| WO | WO 97/09318 | 3/1997 |

OTHER PUBLICATIONS

Chieko Imajo et al., "Evaluation of the Effect of Endothelin–1 and Characterization of the Selective Endothelin a Receptor Antagonist PD155080 in the Prostate," The Journal of Urology, vol. 158, 253–257, Jul. 1997.

Takashi Morita et al., Effects of Endothelin–1 on the Smooth Muscle Contractility of Human Urinary Bladder, Spermatic Cord and Prostatic Adenoma, vol. 84, No. 9, pp. 1649–1653, 1993.

*Primary Examiner*—John M. Ford
(74) *Attorney, Agent, or Firm*—Finnegan, Henderson, Farabow, Garrett & Dunner, L.L.C.

(57) ABSTRACT

A novel agent for prophylaxis or treatment of dysuria, which comprises as an active ingredient a compound of the formula [I]:

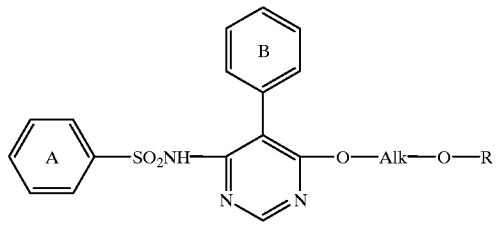

wherein Ring A is a hydroxy-lower alkyl-substituted phenyl group, Ring B is a lower alkyl-substituted phenyl group, Alk is a lower alkylene group, and R is a substituted or unsubstituted nitrogen-containing 6-membered aromatic heteromonocyclic group, or a pharmaceutically acceptable salt thereof, said agent exhibiting an excellent inhibitory activity against the increase in urethral resistance induced by endothelin, and by which being useful in the prophylaxis or treatment of dysuria caused by endothelin.

14 Claims, No Drawings

AGENT FOR PROPHYLAXIS OR TREATMENT OF DYSURIA

This application is a continuation application of PCT international application No. PCT/JP99/01614 which has an international filing date of Mar. 30, 1999 which designated the United States, the entire contents of which are incorporated by reference.

TECHNICAL FIELD

The present invention relates to a novel agent for prophylaxis or treatment of dysuria, more particularly, to an agent for prophylaxis or treatment of dysuria, which comprises as an active ingredient a benzenesulfonamide derivative of the formula [I] as described below.

BACKGROUND ART

With the increase in the population of aged people, prostatic hyperplasia tends to show a yearly increase in numbers thereof, and when prostatic hyperplasia progresses, the prostatic urethral pressure is increased thereby, and as a result, prostatic hyperplasia is accompanied by clinical symptoms such as dysuria. In the current treatment of dysuria accompanying with prostatic hyperplasia, an agent having an activity of lowering the prostatic urethral pressure, for example, an α1 receptor antagonist such as tamsulosin hydrochloride (chemical name: 5-[2-[[2-(ethoxyphenoxy)ethyl]amino]propyl]-2-methoxybenzenesulfonamide hydrochloride) is generally employed.

Recently, various studies have been done as to physiological effects of endothelin on the prostate, and it has been reported that endothelin-1, which is a peptide having a potent vasocontractile activity, exhibits an activity of increasing the prostatic urethral pressure, and that such an activity of endothelin-1 has not been inhibited by an α1 receptor antagonist (cf. Journal of Urology, vol. 158, p. 253, 1997).

There is a report that a cyclic peptide compound of the following formula inhibited the contractions of the smooth muscle of hypertrophied prostatic adenoma induced by endothelin-1 (Journal of Japanese Urology Society, vol. 84, No. 9, p. 1649–54, 1993).

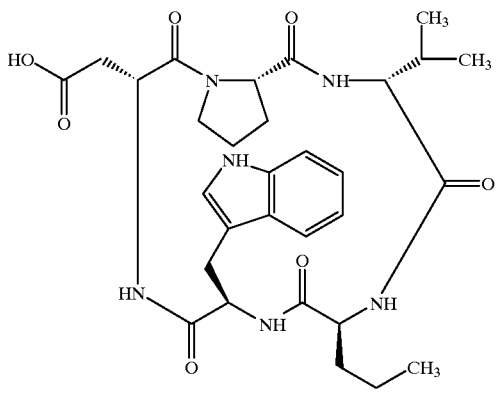

Moreover, it is suggested that a specific phenoxyphenylacetic acid derivative (i.e., N-(4-isopropylbenzenesulfonyl)-α-(4-carboxy-2-n-propylphenoxy)-3,4-methylenedioxyphenylacetamide dipotassium salt) shows an activity of inhibiting the prostatic contractions induced by endothelin-1, and therefore said phenoxyphenylacetic acid compound may be used in the treatment of dysuria accompanying with prostatic hyperplasia (JP-A-8-508034).

On the other hand, the benzenesulfonamide derivative [I] of the active ingredient of the present invention has been known to show an excellent endothelin receptor antagonistic activity and to be useful in the treatment of circulatory diseases such as hypertension, pulmonary hypertension, renal hypertension, Raynaud's disease, myocardial infarction, atherosclerosis, etc. (JP-A-9-59160), but it has not been reported yet that said compound shows an activity of improving dysuria accompanying with prostatic hyperplasia.

DISCLOSURE OF INVENTION

An object of the present invention is to provide a novel agent for prophylaxis or treatment of dysuria, which comprises as an active ingredient a benzenesulfonamide derivative.

The present inventors have intensively studied, and found that some kinds of benzenesulfonamide derivatives effectively inhibit the increase in prostatic urethral pressure induced by endothelin-1, and they have accomplished the present invention.

Namely, the present invention relates to an agent for prophylaxis or treatment of dysuria, which comprises as an active ingredient a compound of the formula [I]:

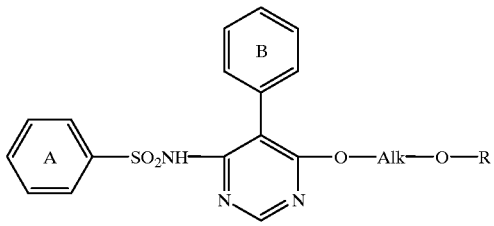

wherein Ring A is a hydroxy-lower alkyl-substituted phenyl group, Ring B is a lower alkyl-substituted phenyl group, Alk is a lower alkylene group, and R is a substituted or unsubstituted nitrogen-containing 6-membered aromatic heteromonocyclic group, or a pharmaceutically acceptable salt thereof.

BEST MODE FOR CARRYING OUT THE INVENTION

In the benzenesulfonamide derivative [I] of the active ingredient of the present invention, the nitrogen-containing 6-membered aromatic heteromonocyclic group is, for example, pyridyl group, pyrimidinyl group, pyrazinyl group, pyridazinyl group, etc. The substituent of said aromatic heterocyclic group is, for example, a halogen atom (e.g., bromine atom, chlorine atom, fluorine atom), and the like.

Examples of the above active ingredient [I] of the present invention are the compounds of the formula [I] wherein Ring A is a hydroxy-$C_{1-6}$ alkyl-substituted phenyl group, Ring B is a $C_{1-6}$ alkyl-substituted phenyl group, Alk is a $C_{1-6}$ alkylene group, and R is a nitrogen-containing 6-membered aromatic heteromonocyclic group (e.g., pyrimidinyl group, etc.) which may optionally be substituted by a halogen atom (e.g., bromine atom, etc.), etc.

Among the above active ingredients, preferable ones are, for example, the compounds of the formula [I] wherein Ring A is a hydroxy-$C_{1-4}$ alkyl-substituted phenyl group (e.g., 2-hydroxy-1,1-dimethylethylphenyl group), Alk is ethylene group, Ring B is a $C_{1-4}$ alkyl-substituted phenyl group (e.g., methylphenyl group), and R is bromopyrimidinyl group.

Among them, especially preferable compound is 4-(2-hydroxy-1,1-dimethylethyl)-N-[6-{2-(5-bromopyrimidin-2-yl-oxy)ethoxy}-5-(4-methylphenyl)pyrimidin-4-yl]benzenesulfonamide or a pharmaceutically acceptable salt thereof (e.g., an alkali metal salt such as sodium salt).

The benzenesulfonamide derivative [I] of the active ingredient of the present invention may clinically be used either in a free form or in the form of a pharmaceutically acceptable salt thereof. The pharmaceutically acceptable salt may be an acid addition salt with an inorganic acid or organic acid, or a salt with an inorganic base, organic base or amino acid, and includes, for example, hydrochloride, sulfate, hydrobromide, methanesulfonate, acetate, fumarate, maleate, oxalate, an alkali metal salt (e.g., sodium salt, potassium salt, etc.), an alkaline earth metal salt (e.g., magnesium salt, calcium salt, etc.), triethylamine salt, and a salt with lysine.

Besides, the benzenesulfonamide derivative [I] or a pharmaceutically acceptable salt of the active ingredient of the present invention thereof may include an internal salt, an adduct, a complex, a hydrate, and a solvate thereof.

The benzenesulfonamide derivative [I] or a pharmaceutically acceptable salt thereof of the active ingredient of the present invention may be administered either orally or parenterally, and can be formulated together with a pharmaceutically acceptable carrier or diluent into a pharmaceutical preparation such as tablets or injections.

The dosage form for oral administration may be solid preparations such as tablets, granules, capsules, powders, or liquid preparations such as solution preparation and suspension preparations. The pharmaceutically acceptable carrier or diluent for oral preparations may be conventional ones, for example, binders (e.g., syrup, acacia gum, gelatin, sorbitol, tragacanth, polyvinylpyrrolidone, etc.), excipients (e.g., lactose, white sugar, corn starch, potassium phosphate, sorbitol, glycine, etc.), lubricants (e.g., magnesium stearate, talc, polyethylene glycol, silica, etc.), disintegrators (e.g., potato starch, etc.), and wetting agents (e.g., sodium laurylsulfate, etc.).

On the other hand, the dosage forms for parenteral administration are preferably injection preparations or drip infusion preparations using distilled water for injection, physiological saline or aqueous glucose solution.

The dose of the benzenesulfonamide derivative [I] or a pharmaceutically acceptable salt thereof of the active ingredient of the present invention may vary according to the administration route, age, weight or conditions of a patient, or severity of the disease to be cured, but the daily dose thereof is usually in the range of about 0.01 mg to 100 mg, preferably in the range of 0.01 mg to 10 mg.

The benzenesulfonamide derivative [I] or a pharmaceutically acceptable salt thereof of the active ingredient of the present invention shows an excellent inhibitory activity against the increase in urethral resistance induced by endothelin, and is useful in the prophylaxis or treatment of dysuria caused by endothelin (e.g., dysuria accompanying with prostatic hyperplasia).

For example, as shown in Experiment 1 as described below, 4-(2-hydroxy-1,1-dimethylethyl)-N-[6-{2-(5-bromopyrimidin-2-yloxy)ethoxy}-5-(4-methylphenyl) pyrimidin-4-yl]benzenesulfonamide sodium salt (1.5 hydrate) completely inhibited the increase in urethral resistance induced by endothelin-1 by intraduodenal administration thereof at a dose of 1 mg/kg in the dogs to which endothelin-1 had intravenously been administered at a dose of 0.4 nmol/kg to increase the urethral resistance.

From the results, the benzenesulfonamide derivatives [I] or a pharmaceutically acceptable salt thereof such as the above compound are useful in the treatment of dysuria caused by endothelin-1.

The benzenesulfonamide derivatives [I] or a pharmaceutically acceptable salt thereof of the active ingredient of the present invention can be prepared, for example, according to the conventional method disclosed in JP-A-9-59160, by reacting a compound of the formula [II]:

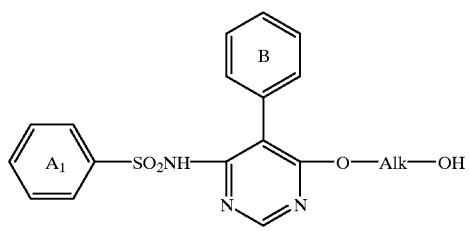

[II]

wherein Ring $A_1$ is a lower alkyl-substituted phenyl group in which the lower alkyl group is substituted by a protected hydroxy group, and the other symbols are as defined above, or a salt thereof (e.g., a salt with an inorganic acid such as hydrochloride, sulfate, an alkali metal salt such as sodium salt, an alkaline earth salt such as calcium salt, etc.), with a compound of the formula [III]:

$X^1$—R [III]

wherein $X^1$ is a reactive residue, and R is as defined above, in the presence of an acid acceptor (e.g., an alkali metal hydride, an alkali metal carbonate, an alkali metal hydroxide, etc.), removing a protecting group (e.g., a conventional protecting group for hydroxy group such as tetrahydropyranyl group, etc.) from the protected hydroxy group on Ring $A_1$ by a conventional method, and if necessary, followed by converting the product into a pharmaceutically acceptable salt thereof.

The reactive reside for $X^1$ of the above compound [III] is, for example, a halogen atom such as chlorine atom, etc.

The reaction between the above compound [II] or a salt thereof with the compound [III] is carried out in a suitable solvent (e.g., tetrahydrofuran, dimethylsulfoxide, dimethylformamide, etc.), at a temperature of from room temperature to 150° C., preferably at a temperature of from room temperature to 100° C.

EXPERIMENT

Inhibitory Activity Against the Increase in Urethral Resistance Induced by Endothelin-1:

Method:

Polyethylene tubes were inserted to male adult mongrel dogs which had been fasted overnight (four dogs, weights: 10 to 14 kg), under pentobarbital anesthesia (30 mg/kg, i.v.), at the femoral veins on both sides. The anesthesia was maintained by continuous transfusion of pentobarbital (4.5 mg/kg) from said polyethylene tubes, and the dogs were ventilated by a respirator for animal (20 strokes per minute, 15 ml/kg/ventilation). Then, a polyethylene tube was inserted for administration of a test compound into the duodenum, and the urinary bladder and the proximal urethra were exposed. In order to avoid the urinary backup within the urinary bladder, a polyethylene tube having a silicon tube was inserted at the ureters on both sides, by which a way for excreting the urine from the body was reserved. Moreover, in order to determine the ventral and dorsal prostatic urethral resistances, the apex of the urinary bladder was incised, and a 2-hole open-tip catheter (12Fr, manufactured by CLINY) was inserted into the prostatic urethra through the bladder body. Said catheter was ligated at the proximal urethra and the bladder body, and one of the ends thereof was connected with a pressure-transducer and a syringe pump (SP-25, manufactured by Terumo Corporation) via a three-way turn-cock. Then, the change in the perfusion pressure (i.e., the change in the urethral resistance, mmHg) caused by the continuous infusion of physiological saline (37° C., 3 ml/hr) through this catheter was recorded on a linearcorder (WR-3701, manufactured by Graphtec Corporation) via a carrier amplifier (AP-621G, manufactured by Nihon Kohden Corporation).

In order to increase the urethral resistance, a solution of phenylephrine (α1 agonist) or endothelin-1 in physiological saline was intravenously administered at a prescribed dose (volume: 0.1 ml/kg) to the dogs when 60 minutes or more elapsed after the above operation.

As a test compound, 4-(2-hydroxy-1,1-dimethylethyl)-N-[6-{2-(5-bromopyrimidin-2-yloxy)ethoxy}-5-(4-methylphenyl)pyrimidin-4-yl]benzenesulfonamide sodium salt 1.5 hydrate was used (it was administered after being dissolved in 5% hydroxypropyl-β-cyclic dextran).

Results:

As shown in Table 1 as described below, phenylephrine (i.v.) dose-dependently increased the prostatic urethral resistance in the anesthetized dogs at a dose of 0.3 μg/kg or more, and the average increase of the prostatic urethral resistance at a dose of 30 μg/kg of phenylephrine was 4.9 mmHg.

On the other hand, as shown in Table 2 as described below, endothelin-1 (i.v.) showed a dose-dependent increasing activity of the prostatic urethral resistance at a dose of 0.05 nmol/kg or more, and it showed the maximum increase of the prostatic urethral resistance at a dose of 0.4 to 0.8 nmol/kg. The activity of endothelin-1 was more long-acting than that of phenylephrine. The average increase of the urethral resistance at a dose of 0.4 nmol/kg of endothelin-1 was 18.9 mmHg, which was about 4 times higher than that of phenylephrine at a dose of 30 μg/kg.

Further, the test compound by intraduodenal administration at a dose of 1 mg/kg completely inhibited the increase in urethral resistance induced by administration of endothelin-1 at a dose of 0.4 nmol/kg. From these results, the benzenesulfonamide derivative [I] or a pharmaceutically acceptable salt thereof of the present invention is useful in the treatment of dysuria accompanying with prostatic hyperplasia.

TABLE 1

URETHRAL RESISTANCE INCREASING ACTIVITY OF PHENYLEPHRINE IN THE ANESTHETIZED DOGS

| Dose (μg/kg) | 0.3 | 1 | 3 | 10 | 30 |
|---|---|---|---|---|---|
| Urethral pressure (mmHg) | 0.8 | 2.1 | 3.3 | 4.6 | 4.9 |

TABLE 2

URETHRAL RESISTANCE INCREASING ACTIVITY OF ENDOTHELIN-1 IN THE ANESTHETIZED DOGS

| Dose (nmol/kg) | 0.05 | 0.1 | 0.2 | 0.4 | 0.8 |
|---|---|---|---|---|---|
| Urethral pressure (mmHg) | 2.2 | 4.5 | 14.3 | 18.9 | 15.4 |

PREPARATION (1) Sodium (35.65 g) is gradually added to ethylene glycol (1.3 liter) at 23–75° C., and thereto is added N-[6-chloro-5-(4-methylphenyl)pyrimidin-4-yl]-4-[2-(2-tetrahydropyranyloxy)-1,1-dimethylethyl]benzenesulfonamide (160 g) at 4° C. The mixture is stirred at 100° C. for 16 hours, and allowed to cool to room temperature. The reaction mixture is poured into a mixture of a saturated aqueous ammonium chloride solution and ethyl acetate under ice-cooling, and the mixture is extracted with ethyl acetate. The extract is washed with a saturated aqueous sodium chloride solution, and the organic layer is dried over anhydrous sodium sulfate and activated carbon. The solid materials are removed by filtration through a Celite pad, and the filtrate is concentrated under reduced pressure. The residue is crystallized from ethyl acetate-diisopropyl ether to give N-[6-(2-hydroxyethoxy)-5-(4-methylphenyl)-pyrimidin-4-yl]-4-[2-(2-tetrahydropyranyloxy)-1,1-dimethyl-ethyl]benzenesulfonamide (80.26 g) as colorless crystals. In addition, the mother liquor is concentrated, and the resultant is recrystallized from ethyl acetate-diisopropyl ether to give the crystals of the above compound (73.1 g).

M.p. 137.0–138.0° C.

(2) The product (80.0 g) obtained in the above (1) is dissolved in a mixture of tetrahydrofuran (330 ml) and dimethylacetamide (132 ml), and the mixture is added dropwise into a suspension of sodium hydride (60% oily dispersion, 17.72 g) in tetrahydrofuran (330 ml) under ice-cooling. To the mixture is added 5-bromo-2-chloropyrimidine (40.0 g, Australian Journal of Chemistry, vol. 17, p. 794, 1964) at the same temperature, and the mixture is stirred at room temperature for 16 hours. The reaction mixture is poured into a mixture of ice and a saturated aqueous ammonium chloride solution, and the mixture is extracted with ethyl acetate. The organic layer is successively washed with water and a saturated aqueous sodium chloride solution, dried over anhydrous sodium sulfate, and subjected to the treatment with activated carbon. The resultant is filtered through a Celite pad to remove the solid materials. The filtrate is concentrated under reduced pressure, and the residue is purified by silica gel column chromatography (eluent; chloroform:ethyl acetate=30:1 to 20:1), and crystallized from ethyl acetate-diisopropyl ether to give N-[6-{2-( 5-bromo-pyrimidin-2-yloxy)ethoxy}-5-(4-methylphenyl)pyrimidin-4-yl]-4-[2-(2-tetrahydropyranyloxy)-1,1-dimethylethyl]benzenesulfonamide (91.83 g) as colorless crystals.

m.p. 138.0–139.0° C.

(3) The product (120 g) obtained in the above (2), p-toluenesulfonic acid monohydrate (39.21 g) and a mixture of tetrahydrofuran (950 ml) and methanol (190 ml) and water (95 ml) are mixed, and the mixture is stirred at room temperature for 17 hours. The reaction mixture thus obtained is further stirred for 3 hours during which the mixture is kept at 40–60° C. The reaction mixture is cooled to room temperature, and thereto is added p-toluenesulfonic acid monohydrate (26.16 g) at room temperature. The mixture is stirred at room temperature for two hours, and thereto is added methanol (250 ml), and refluxed for 15 minutes. The reaction mixture is cooled to room temperature, and thereto is added an aqueous solution of sodium hydrogen carbonate (29.58 g), and the mixture is concentrated under reduced pressure. To the resulting residue are added diisopropyl ether and water, and the precipitated crystals are collected by filtration, dissolved in a mixture of chloroform and tetrahydrofuran, dried over anhydrous sodium sulfate, and concentrated under reduced pressure. The residue is dissolved in methanol, cooled, and the precipitated crystals are collected by filtration to give 4-(2-hydroxy-1,1-dimethylethyl)-N-[6-{2-(5-bromopyrimidin-2-yloxy)ethoxy}-5-(4-methylphenyl)pyrimidin-4-yl]benzenesulfonamide (67.67 g) as colorless crystals.

m.p. 181.0–182.0° C.

(4) To a suspension of the above product (107.0 g) obtained in the above (3) in a mixture of tetrahydrofuran (1000 ml) and methanol (200 ml) is added dropwise a mixture of 28% sodium methoxide in methanol (32.3 g) and methanol (200 ml) in a dry ice-acetone bath over a period of 2 hours. The mixture is concentrated under reduced pressure at 35° C., and methanol is added to the residue. The mixture is refluxed, and the resulting solution is concentrated under reduced pressure until the crystals began to precipitate. The solution is stirred at room temperature for 16 hours, and the precipitated crystals are collected by filtration. The resulting crystals are dried under reduced pressure at 70° C. to give a 0.8 methanolate of 4-(2-hydroxy-1,1-dimethylethyl)-N-[6-{2-(5-bromopyrimidin-2-yloxy)ethoxy}-5-(4-methylphenyl)pyrimidin-4-yl]benzenesulfonamide sodium salt (70.7 g) (m.p. 218–234° C. (decomposed)). Subsequently, the product thus obtained is dried under reduced pressure at 75–80° C. for 4.5 days, and allowed to stand at room temperature under atmospheric pressure overnight to give 4-(2-hydroxy-1,1-dimethylethyl)-N-[6-{2-(5-bromopyrimidin- 2-yloxy)ethoxy}-5-(4-methylphenyl)pyrimidin-4-yl]benzenesulfonamide sodium salt 1.5 hydrate (70.74 g) as colorless crystals.

m.p. 202–243° C. (decomposed); Moisture content (by Karl Fischer's method): 4.34%.

REFERENCE EXAMPLE 1

To a solution of (2-acetoxy-1,1-dimethylethyl)benzene (Journal of Organic Chemistry, vol. 23, p. 920, 1958) in methylene chloride is added dropwise fuming sulfuric acid at 5–20° C., and thereto is further added dropwise thionyl chloride at 10–12° C., and the mixture is stirred at room temperature for 18 hours. The reaction mixture is poured into ice-water, and thereto is added ethyl acetate. The methylene chloride is removed by distillation, and ethyl acetate is added to the residue. The mixture is extracted with ethyl acetate, and the organic layer is washed with an aqueous sodium chloride solution. To the organic layer is added dropwise aqueous ammonia at 10–18° C., and the mixture is stirred at the same temperature for one hour. The reaction mixture is concentrated under reduced pressure, and water is added to the residue. The mixture is acidified with conc. hydrochloric acid, and the precipitated crystals are collected by filtration, washed with water, and concentrated under reduced pressure. The residue is crystallized from chloroform to give the crystals of 4-(2-acetoxy-1,1-dimethylethyl)benzenesulfonamide.

m.p. 156–158° C.

REFERENCE EXAMPLE 2

(1) A mixture of 4,6-dichloro-5-(4-methylphenyl)pyrimidine (10.0 g), 4-(2-acetoxy-1,1-dimethylethyl)benzenesulfonamide (11.58 g), potassium carbonate (14.45 g) and dimethyl-sulfoxide (50 ml) is stirred at 75° C. (bulk temperature) for 3 hours, and thereto is further added 4-(2-acetoxy-1,1-dimethylethyl)benzenesulfonamide (0.34 g). The mixture is stirred at 70–75° C. for 1.5 hour, and the reaction mixture is cooled, and poured into a mixture of ice (100 g) and conc. hydrochloric acid (60 ml). The mixture is extracted with ethyl acetate, and the organic layer is washed, dried, and concentrated under reduced pressure. The residue is crystallized from a mixture of ethyl acetate and diisopropyl ether to give 4-(2-acetoxy-1,1-dimethylethyl)-N-{6-chloro-5-(4-methylphenyl)pyrimidin-4-yl}benzenesulfonamide (14.97 g) as colorless needles.

m.p. 188.0–189.0° C.

(2) The product (20.0 g) obtained in the above (1) is suspended in a mixture of tetrahydrofuran (60 ml) and methanol (60 ml), and thereto is added dropwise a 4N aqueous sodium hydroxide solution (52.8 ml) in an ice-water bath. The mixture is stirred at the same temperature for one hour, and neutralized with conc. hydrochloric acid, and extracted with ethyl acetate. The organic layer is washed, dried and concentrated under reduced pressure. The residue is dissolved in ethyl acetate, and the solution is concentrated under atmospheric pressure. The concentrated solution is diluted with n-hexane, and allowed to stand at room temperature. The precipitated crystals are collected by filtration, and washed to give N-{6-chloro-5-(4-methylphenyl)pyrimidin-4-yl}-4-(2-hydroxy-1,1-dimethylethyl)benzenesulfonamide (17.31 g) as colorless needles.

m.p. 227–228° C.

(3) To a suspension of the product (142.89 g) obtained in the above (2) in methylene chloride are added dihydropyran (39 ml) and camphor-sulfonic acid (1.54 g) at room temperature, and the mixture is stirred at the same temperature for 30 minutes. To the reaction mixture is added a saturated aqueous sodium hydrogen carbonate solution (9 ml), and the solvent is removed by distillation. To the residue is added ethyl acetate (2 liters), and the precipitated crystals are collected by filtration, and washed with water. The above ethyl acetate layer is washed, dried, and concentrated under reduced pressure. The residue and the crystals obtained in the above are combined, and dissolved in a mixture of chloroform and tetrahydrofuran, dried, and concentrated under reduced pressure. The residue is crystallized from a mixture of chloroform and diisopropyl ether to give N-[6-chloro-5-(4-methylphenyl)pyrimidin-4-yl]-4-[2-(2-tetrahydropyranyloxy)-1,1-dimethylethyl]benzenesulfonamide (158.59 g) as colorless crystals.

m.p. 141.0–143.5° C.

INDUSTRIAL APPLICABILITY

The agent for prophylaxis or treatment of dysuria of the present invention shows an excellent inhibitory activity against the increase in urethral resistance induced by endothelin, and hence, it is useful in the prophylaxis or treatment of dysuria caused by endothelin.

What is claimed is:

1. A method for the treatment of dysuria caused by endothelin-1, which comprises administering an effective amount of a compound of the formula (I)

(I)

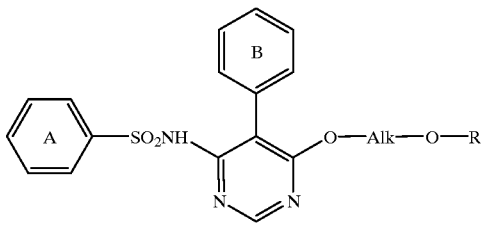

wherein Ring A is a hydroxy-lower alkyl-substituted phenyl group, Ring B is a lower alkyl-substituted phenyl group, Alk is a lower alkylene group, and R is nitrogen-containing 6-membered aromatic heteromonocyclic group selected from the group consisting of a pyridyl group, a pyrimidinyl group, a pyrazinyl group and a pyridazinyl group, which group may optionally be substituted by a halogen atom, or a pharmaceutically acceptable salt thereof to a patient suffering from dysuria or having a possibility thereof.

2. The method for the treatment of dysuria caused by endothelin-1 according to claim 1, wherein the nitrogen-containing 6-membered aromatic heteromonocyclic group is substituted by a halogen atom.

3. The method for the treatment of dysuria caused by endothelin-1 according to claim 1 or claim 2, wherein the nitrogen-containing 6-membered aromatic heteromonocyclic group is a pyrimidinyl group.

4. The method for the treatment of dysuria caused by endothelin-1 according to claim 1, wherein Ring A is a hydroxy-$C_{1-4}$ alkyl-substituted phenyl group, Ring B is a $C_{1-4}$ alkyl-substituted phenyl group, Alk is an ethylene group, and R is a pyrimidinyl group substituted by a bromine atom.

5. The method for the treatment of dysuria caused by endothelin-1 according to claim 1, wherein the compound is 4-(2-hydroxy-1,1-dimethylethyl)-N-[6-{2-(5-bromopyrimidin-2-yloxy)ethoxy}-5-(4-methylphenyl)pyrimidin-4-yl]benzenesulfonamide.

6. The method for the treatment of dysuria caused by endothelin-1 according to claim 1, wherein the effective amount ranges from about 0.01 mg per day to about 100 mg per day.

7. The method for the treatment of dysuria caused by endothelin-1 according to claim 6, wherein the effective amount ranges from about 0.01 mg per day to about 10 mg per day.

8. A method of administering to a patient suffering from or susceptible to dysuria caused by endothelin-1, which comprises administering an effective amount of a compound of the formula (I)

(I)

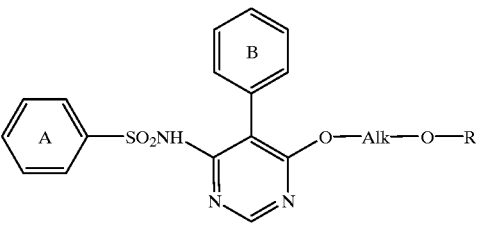

wherein Ring A is a hydroxy-lower alkyl-substituted phenyl group, Ring B is a lower alkyl-substituted phenyl group, Alk is a lower alkylene group, and R is nitrogen-containing 6-membered aromatic heteromonocyclic group selected from the group consisting of a pyridyl group, a pyrimidinyl group, a pyrazinyl group and a pyridazinyl group, which group may optionally be substituted by a halogen atom, or a pharmaceutically acceptable salt thereof to a patient suffering from dysuria or having a possibility thereof.

9. The method of administering to a patient suffering from or susceptible to dysuria caused by endothelin-1 according to claim 8, wherein the nitrogen-containing 6-membered aromatic heteromonocyclic group is substituted by a halogen atom.

10. The method of administering to a patient suffering from or susceptible to dysuria caused by endothelin-1 according to claim 8 or claim 9, wherein the nitrogen-containing 6-membered aromatic heteromonocyclic group is a pyrimidinyl group.

11. The method of administering to a patient suffering from or susceptible to dysuria caused by endothelin-1 according to claim 8, wherein Ring A is a hydroxy-$C_{1-4}$ alkyl-substituted phenyl group, Ring B is a $C_{1-4}$ alkyl-substituted phenyl group, Alk is an ethylene group, and R is a pyrimidinyl group substituted by a bromine atom.

12. The method of administering to a patient suffering from or susceptible to dysuria caused by endothelin-1 according to claim 8, wherein the compound is 4-(2-hydroxy-1,1-dimethylethyl)-N-[6-{2-(5-bromopyrimidin-2-yloxy)ethoxy}-5-(4-methylphenyl)pyrimidin-4-yl]benzenesulfonamide.

13. The method of administering to a patient suffering from or susceptible to dysuria caused by endothelin-1 according to claim 8, wherein the effective amount ranges from about 0.01 mg per day to about 100 mg per day.

14. The method of administering to a patient suffering from or susceptible to dysuria caused by endothelin-1 according to claim 13, wherein the effective amount ranges from about 0.01 mg per day to about 10 mg per day.

* * * * *

UNITED STATES PATENT AND TRADEMARK OFFICE
CERTIFICATE OF CORRECTION

PATENT NO.     : 6,395,741 B1
DATED          : May 28, 2002
INVENTOR(S)    : Kunio Nosaka et al.

It is certified that error appears in the above-identified patent and that said Letters Patent is hereby corrected as shown below:

<u>Column 9,</u>
Lines 41-42, "bromopyrimid in" should be -- bromopyrimidin --.

<u>Column 10,</u>
Line 43, after "hydroxy-" delete the space.

Signed and Sealed this

Twenty-first Day of January, 2003

JAMES E. ROGAN
*Director of the United States Patent and Trademark Office*